(12) United States Patent
Oh et al.

(10) Patent No.: US 6,277,623 B1
(45) Date of Patent: Aug. 21, 2001

(54) **STRAIN *E. COLI* JM83/PKP2 TRANSFORMED WITH A RECOMBI PLASMID AND PHYTASE PRODUCED THEREFROM**

(75) Inventors: Tae Kwang Oh; Young Ok Kim; Hyung Kwoun Kim; Seung Chun Park, all of Daejeon; Dong Kyoo Lee, Seoul; Jung Kee Lee, Daejeon, all of (KR)

(73) Assignees: Daesung Microbiological Labs. Co., Ltd.; Korea Institute of Science and Technology, both of (KR)

( * ) Notice: Subject to any disclaimer, the term of this patent is extended or adjusted under 35 U.S.C. 154(b) by 0 days.

(21) Appl. No.: 09/530,212

(22) PCT Filed: Mar. 21, 1998

(86) PCT No.: PCT/KR98/00056

§ 371 Date: Apr. 27, 2000

§ 102(e) Date: Apr. 27, 2000

(87) PCT Pub. No.: WO98/44125

PCT Pub. Date: Oct. 8, 1998

(30) Foreign Application Priority Data

Mar. 27, 1997 (KR) .................................................. 97-10948

(51) Int. Cl.[7] ........................... C12N 15/70; C12N 15/55; C12N 9/16

(52) U.S. Cl. ................. 435/252.33; 435/196; 435/320.1; 536/23.1; 536/23.2; 536/23.7

(58) Field of Search ..................................... 435/196, 195, 435/252.3, 325, 69.1, 252.33; 536/23.1, 23.2, 23.7

(56) References Cited

FOREIGN PATENT DOCUMENTS

| 420 358 A1 | 4/1991 | (EP) . |
|---|---|---|
| 684 313 A2 | 11/1995 | (EP) . |
| 94/03612 | 2/1994 | (WO) . |

OTHER PUBLICATIONS

Assesion No. AF015775 (1995).*
Accession No. R75410 (1995).*

* cited by examiner

*Primary Examiner*—John L. LeGuyader
*Assistant Examiner*—K. Katcheves
(74) *Attorney, Agent, or Firm*—Finnegan, Henderson, Farabow, Garrett & Dunner, LLP

(57) ABSTRACT

This invention relates to a strain of *E.coli* JM83/pKP2 transformed by a plasmid and phytase produced therefrom, and more particularly, to the strain *E.coli* JM83/pKP2 transformed with a recombinant vector pKP1 or pKP2, so prepared by gene manipulation.

4 Claims, 5 Drawing Sheets

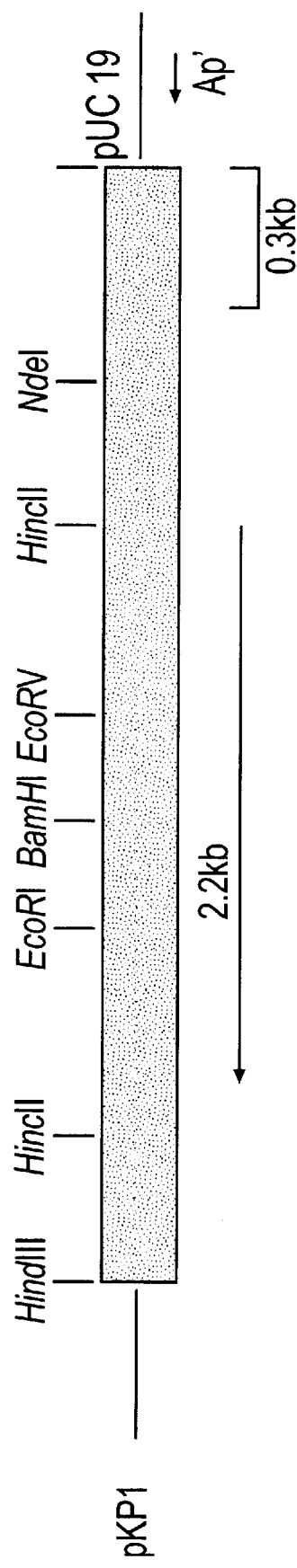
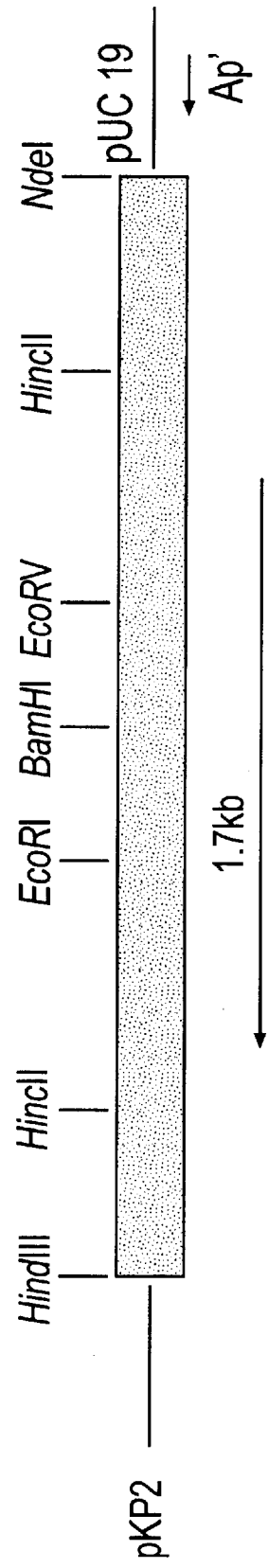

—O— PHYTASE PRODUCED FROM BACILLUS SP.

—◉— PHYTASE PRODUCED FROM E.COLI JM83/-pKP WITHOUT ADDITION OF $Ca^{2+}$

—▣— PHYTASE PRODUCED FROM E.COLI JM83/pKP2 WITH ADDITION OF 5mM $Ca^{2+}$

—O— PHYTASE PRODUCED FROM BACILLUS SP.

—⊙— PHYTASE PRODUCED FROM JM83/pKP2

SEQUENCE LISTING

<160> NUMBER OF SEQ ID NOS: 6

<210> SEQ ID NO 1
<211> LENGTH: 1820
<212> TYPE: DNA
<213> ORGANISM: Bacillus sp.
<220> FEATURE:
<221> NAME/KEY: CDS
<222> LOCATION: (376)..(1524)

<400> SEQUENCE: 1

```
agcagacaag cccgtcaggg cgcgtcagcg ggtgttggcg ggtgtcgggg ctggcttaac      60
tatgcggcat cagagcagat tgtactgaga gtgcaccata tgttgaacaa tttcagcgag     120
ttaatgaaag aaaccaataa atcaaaaatt agagaaaaac attaatctga tgcgctttca     180
tatcgcgtta cccgattaat agaatagaaa ttacaaaata aacattgtac taaatattca     240
ttttaaatat ttgctcacgt caattttttc tcttcataaa tcctcacatt cggacaatct     300
tcacaaaaac ttaacactga acttcctgta tgtattttac aattaaagtg cacgttcata     360
aaaggaggat ggaaa atg aat cat tca aaa aca ctt ttg tta acc gcg gca     411
              Met Asn His Ser Lys Thr Leu Leu Leu Thr Ala Ala
                1               5                   10 gcc gga ttg atg ctc aca tgc ggt gcg gtt tct tct cag gcc aaa cat     459
Ala Gly Leu Met Leu Thr Cys Gly Ala Val Ser Ser Gln Ala Lys His
         15                  20                  25 aag ctg tct gat cct tat cat ttt acc gtg aat gcg gcg gcg gaa acg     507
Lys Leu Ser Asp Pro Tyr His Phe Thr Val Asn Ala Ala Ala Glu Thr
     30                  35                  40 gag ccg gtt gat aca gcc ggt gat gca gct gat gat cct gcg att tgg     555
Glu Pro Val Asp Thr Ala Gly Asp Ala Ala Asp Asp Pro Ala Ile Trp
 45                  50                  55                  60 ctg gac ccc aag aat cct cag aac agc aaa ttg atc aca acc aat aaa     603
Leu Asp Pro Lys Asn Pro Gln Asn Ser Lys Leu Ile Thr Thr Asn Lys
                 65                  70                  75 aaa tca ggc tta gcc gtg tac agc cta gag gga aag atg ctt cat tcc     651
```

```
Lys Ser Gly Leu Ala Val Tyr Ser Leu Glu Gly Lys Met Leu His Ser
             80                  85                  90 tat cat acc ggg aag ctg aac aat gtt gat atc cga tat gat ttt ccg     699
Tyr His Thr Gly Lys Leu Asn Asn Val Asp Ile Arg Tyr Asp Phe Pro
         95                 100                 105 ttg aac gga aaa aaa gtc gat att gcg gcg gca tcc aat cgg tct gaa     747
Leu Asn Gly Lys Lys Val Asp Ile Ala Ala Ala Ser Asn Arg Ser Glu
    110                 115                 120 gga aag aat acc att gag att tac gcc att gac ggg aaa aac ggc aca     795
Gly Lys Asn Thr Ile Glu Ile Tyr Ala Ile Asp Gly Lys Asn Gly Thr
125                 130                 135                 140 tta caa agc att acg gat cca aac cgc ccg att gca tca gca att gat     843
Leu Gln Ser Ile Thr Asp Pro Asn Arg Pro Ile Ala Ser Ala Ile Asp
             145                 150                 155 gaa gta tac ggt ttc agc ttg tac cac agt caa aaa aca gga aaa tat     891
Glu Val Tyr Gly Phe Ser Leu Tyr His Ser Gln Lys Thr Gly Lys Tyr
        160                 165                 170 tac gcg atg gtg aca gga aaa gaa ggc gaa ttt gaa caa tac gaa tta     939
Tyr Ala Met Val Thr Gly Lys Glu Gly Glu Phe Glu Gln Tyr Glu Leu
    175                 180                 185 aat gcg gat aaa aat gga tac ata tcc ggc aaa aag gta agg gcg ttt     987
Asn Ala Asp Lys Asn Gly Tyr Ile Ser Gly Lys Lys Val Arg Ala Phe
190                 195                 200 aaa atg aat tct cag aca gaa ggg atg gca gca gac gat gaa tac ggc    1035
Lys Met Asn Ser Gln Thr Glu Gly Met Ala Ala Asp Asp Glu Tyr Gly
205                 210                 215                 220 agt ctt tat atc gca gaa gaa gat gag gcc atc tgg aag ttc agc gct    1083
Ser Leu Tyr Ile Ala Glu Glu Asp Glu Ala Ile Trp Lys Phe Ser Ala
            225                 230                 235 gag ccg gac ggc ggc agt aac gga acg gtt atc gat cgt gcc gat ggc    1131
Glu Pro Asp Gly Gly Ser Asn Gly Thr Val Ile Asp Arg Ala Asp Gly
        240                 245                 250 agg cat tta acc cct gat att gaa gga ctg acg att tac tac gct gct    1179
Arg His Leu Thr Pro Asp Ile Glu Gly Leu Thr Ile Tyr Tyr Ala Ala
    255                 260                 265 gac ggg aaa ggc tat ctg ctt gcc tca agc cag ggt aac agc agc tat    1227
Asp Gly Lys Gly Tyr Leu Leu Ala Ser Ser Gln Gly Asn Ser Ser Tyr
270                 275                 280 gcg att tat gaa aga cag gga cag aac aaa tat gtt gcg gac ttt cag    1275
Ala Ile Tyr Glu Arg Gln Gly Gln Asn Lys Tyr Val Ala Asp Phe Gln
285                 290                 295                 300 ata aca gac ggg cct gaa aca gac ggc aca agc gat aca gac gga att    1323
Ile Thr Asp Gly Pro Glu Thr Asp Gly Thr Ser Asp Thr Asp Gly Ile
            305                 310                 315 gac gtt ctg ggt ttc ggg ctg ggg cct gaa tat ccg ttc ggt ctt ttt    1371
Asp Val Leu Gly Phe Gly Leu Gly Pro Glu Tyr Pro Phe Gly Leu Phe
        320                 325                 330 gtc gca cag gac gga gag aat ata gat cac ggc caa aag gcc aat caa    1419
Val Ala Gln Asp Gly Glu Asn Ile Asp His Gly Gln Lys Ala Asn Gln
    335                 340                 345 aat ttt aaa atg gtg cca tgg gaa aga atc gct gat aaa atc ggc ttt    1467
Asn Phe Lys Met Val Pro Trp Glu Arg Ile Ala Asp Lys Ile Gly Phe
350                 355                 360 cac ccg cag gtc aat aaa cag gtc gac ccg aga aaa atg acc gac aga    1515
His Pro Gln Val Asn Lys Gln Val Asp Pro Arg Lys Met Thr Asp Arg
365                 370                 375                 380 agc gga aaa taaacatgaa aaaagcagct tatccaagct gcttttttgat            1564
Ser Gly Lys gtgaagagcg tttcatgaga aagtcttgga acggatagcc gtaagcacag ccggcagccg   1624
```

```
gtcatacgtg tacgccggta ctgtctcttg ataattaagc gccgcgattt gtttacgttc    1684
acccgggttt gtcatataaa aatggatctt atccggaaaa tccgcaaacc cgctgtaaga    1744
aacaaatgtt gaaaacgggg gcgcgggaga aggtctgtc agctgaaagg cctgacaagc     1804
cgcaatgtct aagctt                                                    1820
```

<210> SEQ ID NO 2
<211> LENGTH: 383
<212> TYPE: PRT
<213> ORGANISM: Bacillus sp.

<400> SEQUENCE: 2

```
Met Asn His Ser Lys Thr Leu Leu Thr Ala Ala Gly Leu Met
  1               5                  10                  15

Leu Thr Cys Gly Ala Val Ser Ser Gln Ala Lys His Lys Leu Ser Asp
                 20                  25                  30

Pro Tyr His Phe Thr Val Asn Ala Ala Glu Thr Glu Pro Val Asp
             35                  40                  45

Thr Ala Gly Asp Ala Ala Asp Asp Pro Ala Ile Trp Leu Asp Pro Lys
     50                  55                  60

Asn Pro Gln Asn Ser Lys Leu Ile Thr Thr Asn Lys Lys Ser Gly Leu
 65                  70                  75                  80

Ala Val Tyr Ser Leu Glu Gly Lys Met Leu His Ser Tyr His Thr Gly
                 85                  90                  95

Lys Leu Asn Asn Val Asp Ile Arg Tyr Asp Phe Pro Leu Asn Gly Lys
            100                 105                 110

Lys Val Asp Ile Ala Ala Ala Ser Asn Arg Ser Glu Gly Lys Asn Thr
            115                 120                 125

Ile Glu Ile Tyr Ala Ile Asp Gly Lys Asn Gly Thr Leu Gln Ser Ile
            130                 135                 140

Thr Asp Pro Asn Arg Pro Ile Ala Ser Ala Ile Asp Glu Val Tyr Gly
145                 150                 155                 160

Phe Ser Leu Tyr His Ser Gln Lys Thr Gly Lys Tyr Tyr Ala Met Val
                165                 170                 175

Thr Gly Lys Glu Gly Glu Phe Glu Gln Tyr Glu Leu Asn Ala Asp Lys
            180                 185                 190

Asn Gly Tyr Ile Ser Gly Lys Lys Val Arg Ala Phe Lys Met Asn Ser
            195                 200                 205

Gln Thr Glu Gly Met Ala Ala Asp Asp Glu Tyr Gly Ser Leu Tyr Ile
            210                 215                 220

Ala Glu Glu Asp Glu Ala Ile Trp Lys Phe Ser Ala Glu Pro Asp Gly
225                 230                 235                 240

Gly Ser Asn Gly Thr Val Ile Asp Arg Ala Asp Gly Arg His Leu Thr
                245                 250                 255

Pro Asp Ile Glu Gly Leu Thr Ile Tyr Tyr Ala Ala Asp Gly Lys Gly
            260                 265                 270

Tyr Leu Leu Ala Ser Ser Gln Gly Asn Ser Ser Tyr Ala Ile Tyr Glu
            275                 280                 285

Arg Gln Gly Gln Asn Lys Tyr Val Ala Asp Phe Gln Ile Thr Asp Gly
            290                 295                 300

Pro Glu Thr Asp Gly Thr Ser Asp Thr Asp Gly Ile Asp Val Leu Gly
305                 310                 315                 320

Phe Gly Leu Gly Pro Glu Tyr Pro Phe Gly Leu Phe Val Ala Gln Asp
                325                 330                 335
```

-continued

Gly Glu Asn Ile Asp His Gly Gln Lys Ala Asn Gln Asn Phe Lys Met
                340                 345                 350

Val Pro Trp Glu Arg Ile Ala Asp Lys Ile Gly Phe His Pro Gln Val
        355                 360                 365

Asn Lys Gln Val Asp Pro Arg Lys Met Thr Asp Arg Ser Gly Lys
    370                 375                 380

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      phytase peptide
<221> NAME/KEY: MOD_RES
<222> LOCATION: (12)
<223> OTHER INFORMATION: variable amino acid

<400> SEQUENCE: 3

Ser Asp Pro Tyr His Phe Thr Val Asn Ala Ala Xaa Glu Thr Glu
 1               5                  10                  15

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      phytase peptide
<221> NAME/KEY: MOD_RES
<222> LOCATION: (2)
<223> OTHER INFORMATION: variable amino acid

<400> SEQUENCE: 4

Ala Xaa Asp Asp Glu Tyr Gly Ser Ser Leu Tyr
 1               5                  10

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (6)
<223> OTHER INFORMATION: represents a, t, c or g

<400> SEQUENCE: 5
gayccntayc aytty                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (1)
<223> OTHER INFORMATION: represents a, t, c or g

<400> SEQUENCE: 6
nccrtaytcr tcrtc                                                    15

STRAIN E. COLI JM83/PKP2 TRANSFORMED WITH A RECOMBI PLASMID AND PHYTASE PRODUCED THEREFROM

BACKGROUND OF THE INVENTION

1. Field of the Invention

This invention relates to a strain *E.coli* JM83/pKP2 transformed with a novel plasmid and phytase produced therefrom and, more particularly, to a strain *E.coli* JM83/pKP2 transformed with a novel recombinant vector pKP1 or pKP2, so prepared by a gene manipulation, through elucidating the gene sequence intended for the mass production of novel phytase serving the role to enhance the phosphorous bioavailability in grains used as livestock feeds.

2. Description of the Prior Art

Phytase is an enzyme which degrades phytic acid into phosphate and phosphate inositol. 50~70% of phosphate in grain used as livestock feeds exists in the form of phytic acid, but phytase is not present in monogastric animals such as hens and hogs, thus resulting in low phosphate availability. Further, indigested phytic acid phytate released to a water source has become one of the serious environment contamination sources and causes eutrophication in small lakes or tides. Further, monogastric animals can not utilize phytic acid in their intestine due to its chelation with a trace amount of minerals, amino acids and vitamins which are essential for the metabolism of livestock. These formed water insoluble and indigestible chelate-complexes released in the form of feces are responsible for the change of the environmental ecosystem, thus inducing a serious environmental contamination.

In view of these situations, the application of phytase into the livestock feeds can reduce the supply of inorganic phosphate due to an increase of phosphate bioavailability in livestock, thus leading to economic benefits. In addition, the improved availability of phosphate and other bioactive substances may also contribute much to the reduction of the environmental contamination.

In particular, the utilization of phytase in livestock is very important in that the law regulating the amount of phosphate in animal waste was established in 1996 in Korea and, in addition to that, it has been mandatory to add phytase in the feeds of animals in the European countries. Further, when phytase i added to the feeds, it may greatly improve the productivity of livestock by enhancing the availability of some bioactive substances such as vitamins and amino acids, including some trace elements such as calcium and zinc ions whose activity is reduced by chelation with negatively charged phytate. As such, the use of feeds containing phytase in livestock can enhance the availability of feeds and reduce the environmental contamination cause by phosphate.

From the aforementioned benefits, the intensive studies with respect to phytase including the effects of phytase on animals (L. G. Yound et al., 1993; X. G. Lei et al., 1994; Z. Morez et al., 1994) have been performed mainly in Europe (A. H. J. Ullah et al., 1994; K. C. Ehrich, 1994; C. S. Piddington, 1993). However, since phytase can cleave a limited number of phosphate only and is mostly produced by molds which have slow growth rate, it is not economical in terms of mass production. In addition, it is difficult to use the phytic acid as an additive for monogastric animals since it is undesirable for their physiological characteristics.

The inventor, et al. have performed intensive studies for overcoming the above problems associated with phytase. As a result, a novel strain Bacillus sp. DS-11 producing phytase with an excellent activity and different characteristics over the conventional phytase was identified and deposited to the Korean Collection for Type Cultures within the Korea Research Institute of Bioscience and Biotechnology affiliated with Korea Institute of Science and Technology (KCTC 0231BP), the Korean Patent Strain Depository Institute. The above patent application was filed with the Korean Industrial Patent Office (The Korean Patent Appl. No.: 96-6817). Hence, various characteristics on a novel phytase produced from the microorganism were investigated and, as a result, the novel phytase proved to be excellent on heat and pH with better stability.

From the above results, the inventor et al. sequenced the DNA by cloning some phytase-coding gene in a strain Bacillus sp. DS-11 under the patent application so as to ensure the mass production of a novel phytase having the above excellent characteristics. As a result, the phytase-coding gene sequence Bacillus sp. DS-11 was recognized to be a novel one, being entirely different from that of *Aspergillus awamori*(WO 94-3072A), *Aspergillus ficum* (EP 42038, U.S. Pat. No. 5,436,156), *Aspergillus niger*(EP 420358) and *Aspergillus terreus*(EP 684313) among the genes clones hitherto. Thus, its accessory No. U85968(date Jan. 21, 1997) was given from GenBank of NCBI in the U.S.A.

Next, the inventor et al. transformed *E.coli* with the plasmid vector (pKP1 or pKP2 ) encoding the phytase gene of Bacillus sp. DS-11, and the transformed strain *E.coli* JM83/pKP2 was deposited at the Korean Collection Type Cultures within the Korea Research Institute of Bioscience and Biotechnology affiliated with the Korea Institute of Science and Technology (KCTC 0308BP dated Jan. 28, 1997), the Korean Patent Strain Depository Institute.

SUMMARY OF THE INVENTION

Therefore, an object of this invention is to provide a plasmid vector pKP1 and pKP2 for transformation intended for mass production of phytase, a transformed strain *E.coli* JM83/pKP2 (KCTC 0308BP) herewith, and a process of mass production of phytase from said strain.

DESCRIPTION OF THE DRAWINGS

FIG. 1*a* shows the subcloning and mapping of pKP1 by restriction enzyme;

FIG. 1*b* shows the subcloning and mapping of pKP2 by restriction enzyme;

Figure 2:
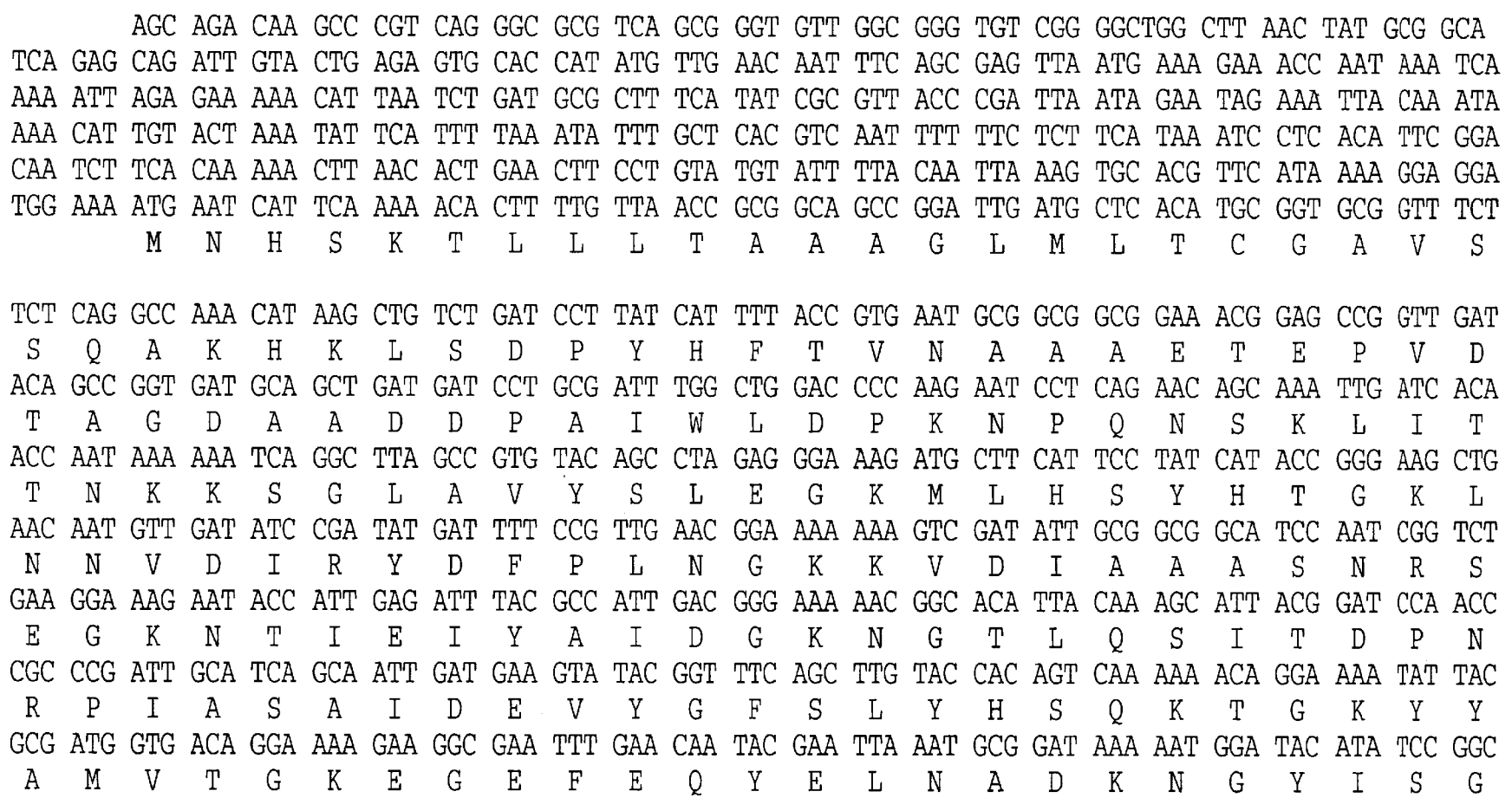
Figure 2:
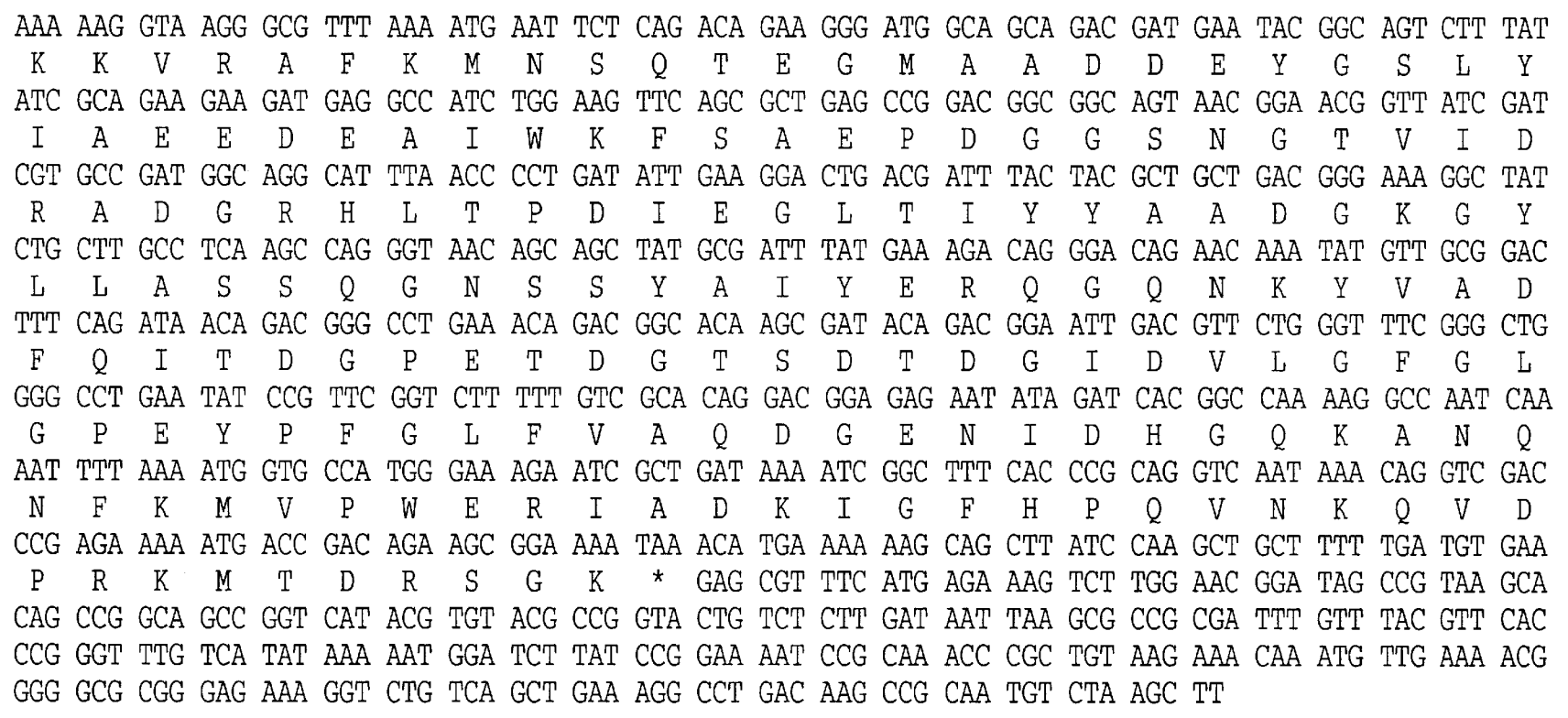

FIG. 2 shows the base sequence and the estimated amino acid sequence of phytase DS-11;

DETAILED DESCRIPTION OF THE INVENTION

Figure 3A:
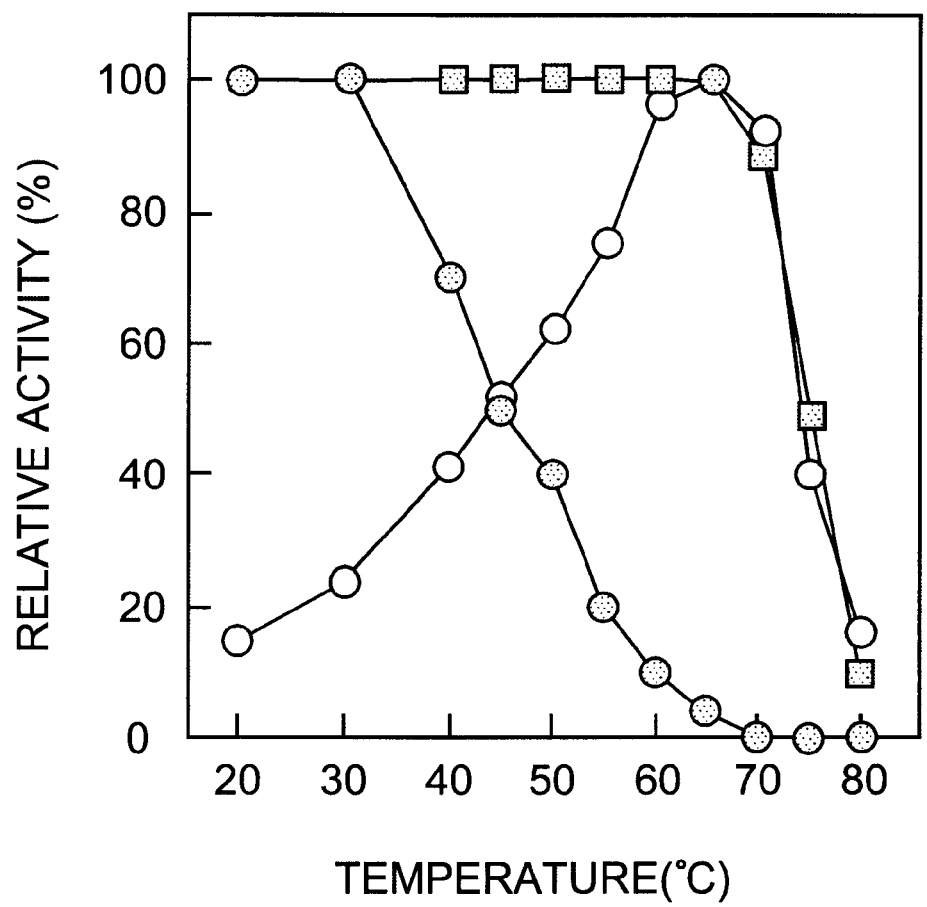
FIG. 3*a* shows the relative activity of phytase DS-11, produced from a transformed strain *E.coli* JM83/pKP2, on heat.

This invention relates to a novel phytase from Bacillus sp. DS-11 and characterized by DNA base sequence of the sequence table 1 or amino acid sequence of the sequence table 2.

Also, this invention includes plasmid pKP1 or pKP2 containing DNA of sequence table 1, which is ligated in such a manner and expressed in *E.coli*.

Further, this invention includes a novel strain *E.coli* JM83/pKP2 (KCTC 0308BP) transformed with plasmid pKP1 or pKP2 containing the phytase-coding gene of the sequence table 1.

This invention is explained in more detail as set forth hereunder

According to this invention, the phytase-coding gene obtained from Bacillus sp. DS-11 is inserted into a plasmid pUC19 vector to prepare a novel recombinant DNA expression vector pKP1 or pKP2. After culturing *E.coli* JM-83 cloned by recombinant DNA expression vector, some colonies with effective expression potency are selected and then used for the mass production of phytase via cultivation of such colonies. Further, only pKP1 or pKP2, the recombinant DNA expression vector, is isolated from the colonies to determine its DNA sequence.

This invention is explained in more detail by the following steps.

Preparation of Novel Plasmid pKP1 and pKP2

(1) Sequencing of N-terminal amino acid

Purified phytase protein was applied to SDS-polyacrylamide gel electrophoresis (SDS-PAGE) and transferred to PVDF membrane(Bio-Rad Lab). Then the electroblotting was performed using 10 mM CAPS(3-cyclohexylamino-1-propanesulfonic acid) buffer solution containing 10% methanol under pH 11.0, 4° C. and 400 mA for 45 hours. After cleaving the desired protein band only, it was analyzed by the Edman method using a protein/peptide sequencer [Applied Biosystems model 476A Protein/Peptide Sequencer(Applied Biosystems Ins., CA, USA)]. N-terminal amino acid sequence of purified phytase protein:

Ser-Asp-Pro-Tyr-His-Phe-Thr-Val-Asn-Ala-Ala-X-Glu-Thr-Glu (SEQ ID NO:3)

(2) Amino acid sequencing of inner peptide

Purified phytase protein was added to 70% formic acid to 1% (w/v) concentration, and with the addition of about 100-fold mass of CNBr, the mixture was reacted at room temperature for 24 hours. Then, 100-fold water was added to the reacting solution, and the reaction was discontinued. Using the same procedure as described in the above (1), electrophoresis was carried out to determine the amino acid sequence of inner peptide N-terminal amino acid sequence of internal protein fragments of phytase cleaved with CNBr;

Ala-X-Asp-Asp-Glu-Tyr-Gly-Ser-Ser-Leu-Tyr  (SEQ ID NO:4)

(3) Preparation of oligonucleotide probe

Oligonucleotide probe was designed based on the amino acid sequence obtained in the procedure as described in the above (1) and (2), and synthesized with DNA synthesizer (Applied Biosystems ABI380B).

With oligonucleotide, so synthesized by the above method as a primer and chromosomal DNA of DS-11 as template DNA as well as Taq DNA polymerase and dNTP in use, polymerase chain reaction(PCR) was carried out under the following conditions:

① Denaturation: 95° C. for one minute
② Annealing: 50° C. for one minute
③ Polymerization: 72° C. for one minute
④ Post-elongation: 72° C. for 7 minutes Under the above condition, the PCR was carried out and followed by 1.5% agarose gel electrophoresis to obtain 600-bp PCR product. After recovering the PCR product from the gel, it was used as a probe.

Oligonucleotide probe based on N-terminal amino acid sequence;

Amino acid sequence:

```
        1   2   3   4   5   6   7   8   9   10  11  12  13  14  15
        Ser-Asp-Pro-Tyr-His-Phe-Thr-Val-Asn-Ala-Ala-X-Glu-Thr-Glu      (SEQ ID NO:3)

Possible combination of codons: 5'GAT-CCT-TAT-CAT-TTT3'        (SEQ ID NO:5)
                                           C    C   C   C   C
                                                            G
                                                            A
```

Oligonucleotide probe based on N-terminal amino acid sequence of internal protein fragments:

Amino acid sequence:

```
        1   2  3   4   5   6   7   8   9   10  11
        Ala-X-Asp-Asp-Glu-Tyr-Gly-Ser-Ser-Leu-Tyr                      (SEQ ID NO:4)

Possible combination of codons: 3'CTA-CTA-CTT-ATA-CCA5'        (SEQ ID NO:6)
                                           G    G   C   G   G
                                                            T
                                                            C
```

(4) Hybridization of DS-11 genomic DNA

Chromosomal DNA derived from Bacillus sp. DS-11 was isolated by the Marmur method(Marmur J. 1961, Mol Biol. 3, 208). To ascertain whether the oligonucleotide probe prepared by the above (3) was appropriate in the screening of genomic library, genomic DNA cleaved with several restriction enzymes was applied to agarose gel electrophoresis and then transferred to the nylon membrane. Then, with DIG DNA labeling a detection kit (Boehringer Mannheim, Germany)] as well as 600-bp DNA fragments as a probe, so synthesized from the above (3), southern hybridization was performed. As a result, it was confirmed that when HindIII, Cla I and PstI were applied, the gene showed a positive signal at 2.2 kb, 4 kb and 6 kb, respectively When the genomic library of Bacillus sp. DS-11 was prepared, therefore, restriction enzyme HindIII was employed.

(5) Screening for the phytase-coding gene

Chromosomal DNA of Bacillus sp. DS-11 was cleaved with HindIII and then, 3–5 kb DNA fragments were screened. Such DNA fragments were also cleaved with HindIII, ligated to vector pUC19 treated with phosphatase (CIP) and introduced into the competent *E.coli* JM83. Such transformed strain was cultured in LB(Luria-Bertani) plate containing 100 μg/ml of ampicillin at 37° C. for 16 hours and transferred to the nylon membrane. Further, the strain was under colony hybridization with DNA oligonucleotide probe, so synthesized from the (3), to select some colonies representing the signal. In order to identify whether phytase gene of Bacillus sp. DS-11 was properly introduced into the host, the phytase activity was measured by the Fiske method (Fiske C. H. and Subbarow Y. P., J.Biol. Chem. 1925,66, 375). As a result, 2 colonies having the signal could be obtained among 10,000 colonies. They were cultured and then plasmids, 4.9-kb in size joined by 2.2-kb insert DNA, were isolated. And such plasmid was named as pKP1. In addition, it was ascertained that pKP1 contained phytase gene properly inserted through measuring the expression potency of phytase.

(6) Mapping and subcloning using a restriction enzyme

As a result of cleaving 4.9kb pKP1 with several restriction enzymes, it was confirmed to be some restriction sites of EcoRI, BamHI, NdeI, HincII and EcoRV within 2.2-kb insert DNA. To find out the genes only necessary for the expression of enzyme potency, the subcloning of the pKP1 plasmid was carried out (FIG. 1a). pKP1 and pUC19 were cleaved with HindIII and Ndel, respectively, joined each other. Such plamid vector was introduced into *E.coli* JM83so that *E.coli* JM83with 4.4-kb pKP2 containing 1.7 kb-insert DNA might be obtained(FIG. 1b).

Transformation Process of Strain

Chromosomal DNA of Bacillus sp. DS-11 was cleaved with HindIII and then, 3–5 kb DNA fragments was selected. Such DNA fragments were also cleaved with HindIII, ligated to vector pUC19 treated with phosphatase (CIP) to obtain a novel plasmid pKP1 or pKP2. To express such plasmid into phytase, it was introduced into the competent *E.coli* JM83as a host. Thus, the transformed strain, was named as *E.coli* JM83/pKP2 and deposited to the Korean Collection for Type Cultures within the Korea Research Institute of Bioscience and Biotechnology affiliated to the Korea Institute of Science and Technology dated Jan. 28, 1997 (the accession No.: KCTC 0308BP).

The bacteriological, cultural and microbiological characteristics of the transformed strain were studied, and all results were the same as that of *E.coli* except for the production capability of phytase.

Isolation and Purification of Phytase Produced from the Transformed Strain

The novel strain *E.coli* JM83/pKP2, so transformed, was cultured in LB liquid medium containing 100 μg/ml of ampicillin at 37° C., centrifuged and recovered. The recovered microorganism was dissolved in the Tris buffer solution (10 mM,pH 7.0) containing 5 mM $CaCl_2$ and sonicated for 1 hour using Sonifier 450. Then, the sonicated microorganism was re-centrifuged, and its supernatants were used as crude enzyme solution. The protein saturated with 50% acetone was isolated on Fast Protein Liquid Chromatography (FPLC consisting of open column of phenyl sepharose CL-4B and Resource S superose 12HR 10/30 column), the same enzyme as phytase produced from Bacillus sp. DS-11 prior to gene manipulation could be isolated.

Measurement of Phytase Potency Produced from the Transformed Strain]

(1) Measurement of phytase potency

The novel strain *E.coli* JM83/pKP2, so transformed, was cultured in LB agar (Luria-Bertani) plate containing 100 μg/ml of ampicillin at 37° C. for 16 hours and transferred to the nylon membrane. The strain was applied to colony hybridization with DNA oligonucleotide probe, so synthesized in the above (3), so as to examine the colonies representing the signal. To ascertain whether phytase-coding gene of Bacillus sp. DS-11 was properly introduced into *E.coli* JM83, the phytase potency was measured by the Fiske method(Fiske C. H. and Subbarow Y. P., J.Biol. Chem. 1925,66, 375). As a result, the transformed strains having complete enzymatic activity were selected.

(2) Comparison on activity and stability of phytase on heat and pH including its molecular weight To ascertain whether phytase produced from the transformed strain *E.coli* JM83/pKP2 was the same as that phytase produced from the original strain, the activity and stability on heat and pH of phytase were compared. To measure its stability on heat, each phytase was left at predetermined temperature for 10 minutes in the same method and then its residual activity measured. As shown in FIG. 3a. when calcium ion ($Ca^{2+}$) was not added into the phytase-containing solution, the activity of phytase began to reduce at 40° C., while in case of adding 5 mM calcium ion, it was stabilized up to 70° C. and its activity was maintained by 50% even at 90° C.

Figure 3B:
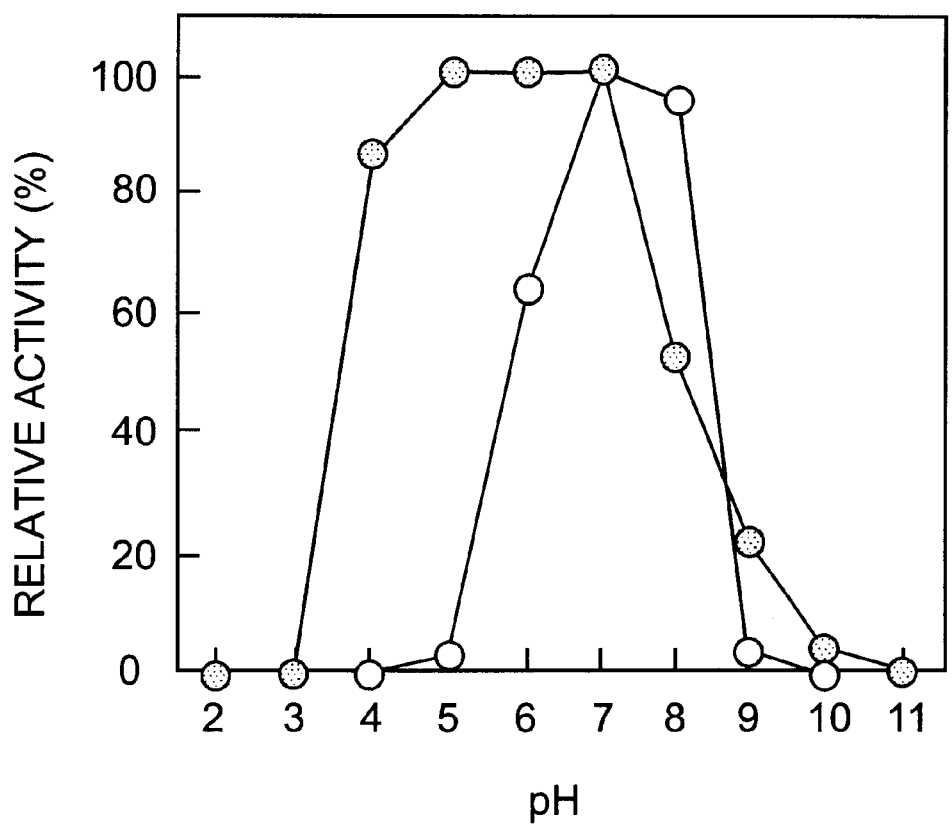
FIG 3*b* shows the relative activity of phytase DS-11, produced from a transformed strain *E.coli* JM83/pKP2, on pH.

Also, FIG. 3b shows the phytase activity depends on pH and the optimum pH of both phytases is 7.0. Further, to identify its stability on pH, each phytase was left at different values of pH for 1 hour and followed to measure its residual activity, respectively. Even at acidic condition of less than pH 4, both phytases showed significant enzymatic activity and thus, it was considered that they may be stabilized in the stomach.

Besides, both phytases have the same molecular weight of 43,000 Dalton.

From the above results, it was considered that phytase produced from the transformed strains was the same as one produced from the original one (Bacillus sp. DS-11).

DNA Sequencing of Phytase-coding Gene

To sequencing 1.7-kb insert DNA within pKP2, after deletion subclones in several different sizes were obtained based on restriction site. The DNA fragment of the total 1.7-kb was prepared from them with PCR using forward and reverse primers. And then, the open reading frame (ORF) of phytase consisting of 1149 nucleotides (383 amino acids) was sequenced using MacMolly 3.5 program and as a result, it was ascertained that the above phytase coincided with N-terminal amino acid of phytase 15 amino acids) isolated from Bacillus sp. DS-11 strain (FIG. 2). Further, it was considered that this was a novel phytase, being entirely different from that produced from the conventional Aspergillus sp. strains. As a result of analyzing its amino acid sequence, 80% between 175 amino acids of C-terminal of this invention and gene of operon regulated by the Sporulation Regulatory Protein of *Bacillus subtilis* was coincided.

Sequence Table 1

Sequence length: 1149

Type of sequence: Nucleic acid

Number of Chain: Double helix

Shape: Linear

Sequence type: Genomic DNA

Origin:
  Name of species: Bacillus sp.
  Name of strain: DS-11
Features of sequence:
  Signal representing the features: CDS
  Location of presence: 377. . . 1526
  Method to determine the features: E Signal representing the features: sig peptide
  Location of presence: 377. . . 466
  Method to determine the characteristics: E Signal representing the characteristics: mat peptide
  Location of presence: 467. . . 1526
  Method to determine the characteristics: E

```
         10         20         30         40         50         60       Sequence 1
ATGAATCATT CAAAAACACT TTTGTTAACC GCGGCAGCCG GATTGATGCT CACATGCGGT

GCGGTTTCTT CTCAGGCCAA ACATAAGCTG TCTGATCCTT ATCATTTTAC CGTGAATGCG

GCGGCGGAAA CGGAGCCGGT TGATACAGCC GGTGATGCAG CTGATGATCC TGCGATTTGG

CTGGACCCCA AGAATCCTCA GAACAGCAAA TGATCACAA CCAATAAAAAA ATCAGGCTTA

GCCGTGTACA GCCTAGAGGG AAAGATGCTT CATTCCTATC ATACCGGGAA GCTGAACAAT

GTTGATATCC GATATGCTTT TCCGTTGAAC GGAAAAAAAG TCGATATTGC GGCGGCATCC

AATCGGTCTG AAGGAAACAA TACCATTGAG ATTTACGCCA TTGACGGGAA AAACGGCACA

TTACAAAGCA TTACGGATCC AAACCGCCCG ATTGCATCAG CAATTGATGA AGTATACGGT

TTCAGCTTGT ACCACAGTCA AAAAACAGGA AAATATTACG CGATGGTGAC AGGAAAAGAA

GGCGAATTTG AACAATACGA ATTAAATGCG GATAAAAATG GATACATATC CGGCAAAAAG

GTAAGGGCGT TTAAAATGAA TTCTCAGACA GAAGGGATGG CAGCAGACGA TGAATACGGC

AGTCTTTATA TCGCAGAAGA AGATGAGGCC ATCTGGAAGT TCAGCGCTGA GCCGGACGGC

GGCAGTAACG GAACGGTTAT CGATCGTGCC GATGGCAGGC ATTTAACCCC TGATATTGAA

GGACTGACGA TTTACTACGC TGCTGACGGG AAAGGCTATC TGCTTGCCTC AAGCCAGGGT

AACAGCAGCT ATGCGATTTA TGAAAGACAG GGACAGAACA AATATGTTGC GGACTTTCAG

ATAACAGACG GGCCTGAAAC AGACGGCACA AGCGATACAG ACGGAATTGA CGTTCTGGGT

TTCGGGCTGG GGCCTGAATA TCCGTTCGGT CTTTTTGTCG CACAGGACGG AGAGAATATA

GATCACGGCC AAAAGGCCAA TCAAAATTTT AAAATGGTGC CATGGGAAAG AATCGCTGAT

AAAATCGGCT TCACCCGCA GGTCAATAAA CAGGTCGACC CGAGAAAAAT GACCGACACA

AGCGGAAAAT AA
```

Sequence Table 2

Sequencing length:383
Sequencing form: amino acid
Shape: Linear
Sequence type: protein

```
 1   2   3   4   5   6   7   8   9   10    Sequence
Met Asn His Ser Lys Thr Leu Leu Leu Thr Ala Ala Ala Gly Leu Met Leu Thr Cys Gly Ala Val Ser Ser Glu Ala Lys His Lys Leu Ser Asp Pro Tyr His Phe Thr Val Asn Ala Ala Ala Gln Thr Gln Pro Val Asp Thr Ala Gly Asp Ala Ala Asp Asp Pro Ala Ile Trp Leu Asp Pro Lys Asn Pro Glu Asn Ser Lys Leu Ile Thr Thr Asn Lys Lys Ser Gly Leu Ala Val Tyr Ser Leu Gln Gly Lys Met Leu His Ser Tyr His Thr Gly Lys Leu Asn Asn Val Asp Ile Arg Tyr Asp Phe Pro Leu Asn Gly Lys Lys Val Asp Ile Ala Ala Ala Ser Asn Arg Ser Gln Gly Lys Asn Thr Ile Gln Ile Tyr Ala Ile Asp Gly Lys Asn Gly Thr Leu Glu Ser Ile Thr Asp Pro Asn Arg Pro Ile Ala Ser Ala Ile Asp Gln Val Tyr Gly Phe Ser Leu Tyr His Ser Glu Lys Thr Gly Lys Tyr Try Ala Met Val Thr Gly Lys Gln Gly Gln Phe Gln Glu Tyr Gln Leu Asn Ala
```

-continued

| | | | | | | |
|---|---|---|---|---|---|---|
| Asp | Lys | Asn Gly Tyr Ile Ser Gly Lys Lys | | | | |
| Val | Arg | Ala Phe Lys Met Asn Ser Glu Thr | | | | |
| Gln | Gly | Met Ala Ala Asp Asp Gtn Tyr Gly | | | | |
| Ser | Leu | Tyr Ile Ala Gtn Gln Asp Gln Ala | | | | |
| Ile | Trp | Lys Phe Ser Ala Gln Pro Asp Gly | | | | |
| Gly | Ser | Asn Gly Thr Val Ile Asp Arg Ala | | | | |
| Asp | Gly | Arg His Leu Thr Pro Asp Ile Gln | | | | |
| Gly | Leu | Thr Ile Tyr Tyr Ala Ala Asp Gly | | | | |
| Lys | Gly | Tyr Leu Leu Ala Ser Ser Glu Gly | | | | |
| Asn | Ser | Ser Tyr Ala Ile Tyr Gln Arg Glu | | | | |
| Gly | Glu | Asn Lys Tyr Val Ala Asp Phe Glu | | | | |
| Ile | Thr | Asp Gly Phe Gln Thr Asp Gly Thr | | | | |
| Ser | Asp | Thr Asp Gly Ile Asp Val Leu Gly | | | | |

-continued

Phe Gly Leu Gly Pro Gln Tyr Pro Phe Gly

Leu Phe Val Ala Glu Asp Gly Gln Asn Ile

Asp His Gly Glu Lys Ala Asn Glu Asn Phe

Lys Met Val Pro Trp Gln Arg Ile Ala Asp

Lys Ile Gly Phe His Pro Glu Val Asn Lys

Glu Val Asp Pro Arg Lys Met Thr Asp Arg

Ser Gly Lys

This invention has the advantages of economy with respect to the preparation of phytase in a large-scale since a recombinant DNA expression vector is prepared using the sequences of DNA and amino acid in such a manner as elucidated in the above and may be introduced into other living organisms having a rapid growth rate and easily regulatable to produce phytase having excellent activity and characteristics.

What is claimed is:

1. A plasmid having the DNA sequence as set forth in SEQ ID NO: 1.

2. *E.coli* JM83/pKP2 transformed with a plasmid having the DNA sequence as set forth in SEQ ID NO:1.

3. An isolated phytase produced from the strain *E.coli* JM83/pKP2.

4. The phytase, according to claim 3, wherein said phytase has an amino acid sequence as set forth in SEQ ID NO: 2.

* * * * *